(12) United States Patent
Ubukata

(10) Patent No.: US 10,605,747 B2
(45) Date of Patent: Mar. 31, 2020

(54) RADIOGRAPHIC IMAGE CAPTURING SYSTEM

(71) Applicant: KONICA MINOLTA, INC., Chiyoda-ku, Tokyo (JP)

(72) Inventor: Kenroku Ubukata, Hachioji (JP)

(73) Assignee: KONICA MINOLTA, INC., Tokyo (JP)

( * ) Notice: Subject to any disclaimer, the term of this patent is extended or adjusted under 35 U.S.C. 154(b) by 430 days.

(21) Appl. No.: 15/452,806

(22) Filed: Mar. 8, 2017

(65) Prior Publication Data

US 2017/0292921 A1    Oct. 12, 2017

(30) Foreign Application Priority Data

Apr. 8, 2016    (JP) .................................. 2016-077892

(51) Int. Cl.
*A61B 6/00*    (2006.01)
*G01N 23/04*    (2018.01)
(Continued)

(52) U.S. Cl.
CPC ............. *G01N 23/04* (2013.01); *A61B 6/548* (2013.01); *A61B 6/566* (2013.01); *A61B 6/582* (2013.01);
(Continued)

(58) Field of Classification Search
None
See application file for complete search history.

(56) References Cited

U.S. PATENT DOCUMENTS

| 6,510,202 | B2 * | 1/2003 | Tamura | ..................... A61B 6/06 378/154 |
| 6,782,077 | B2 * | 8/2004 | Hirai | ....................... A61B 6/06 378/154 |

(Continued)

FOREIGN PATENT DOCUMENTS

| JP | 2012029920 A | 2/2012 |
| JP | 2013223535 A | 10/2013 |

OTHER PUBLICATIONS

Japanese Office Action (and English language translation thereof) dated Feb. 12, 2020 issued in Japanese Application No. 2017-077892.

*Primary Examiner* — Thomas R Artman
(74) *Attorney, Agent, or Firm* — Holtz, Holtz & Volek PC

(57) ABSTRACT

A radiographic image capturing system includes: a radiation irradiating apparatus which emits radiation and provides notification of radiation emission while emitting the radiation; a radiographic image capturing apparatus which includes two-dimensional matrix radiation detecting elements and reads electric charges accumulated in the radiation detecting elements as image data; an exposure switch capable of two-step manipulations, the exposure switch transmitting an activation signal in response to a first-step manipulation and transmitting a radiation start signal in response to a second-step manipulation; a signal transceiver which receives the activation signal and transfers the received activation signal to the radiation irradiating apparatus; and a delay time calculating device which calculates, as a delay time, a difference between a time of reception of the activation signal at the signal transceiver and a time of start of the notification of radiation emission at the radiation irradiating apparatus.

6 Claims, 10 Drawing Sheets

(51) Int. Cl.
*H04N 5/32* (2006.01)
*G01T 1/17* (2006.01)
(52) U.S. Cl.
CPC ............... *A61B 6/585* (2013.01); *G01T 1/17* (2013.01); *H04N 5/32* (2013.01)

(56) References Cited

U.S. PATENT DOCUMENTS

| | | | |
|---|---|---|---|
| 7,006,600 B1* | 2/2006 | Krema | A61B 6/145 348/E5.086 |
| 7,844,031 B2* | 11/2010 | Newman | A61B 6/4233 378/114 |
| 7,974,382 B2* | 7/2011 | Kitano | G01N 23/04 378/114 |
| RE42,793 E* | 10/2011 | Tamura | A61B 6/06 378/154 |
| RE42,852 E* | 10/2011 | Tamura | A61B 6/06 378/154 |
| 8,085,901 B2* | 12/2011 | Newman | A61B 6/4233 378/114 |
| 8,611,500 B2 | 12/2013 | Tsuchiya | |
| 8,687,767 B2* | 4/2014 | Newman | A61B 6/4233 378/102 |
| 8,835,859 B2* | 9/2014 | Tsuchiya | H01L 31/08 250/363.01 |
| 8,948,342 B2 | 2/2015 | Tsuchiya | |
| 9,097,643 B2* | 8/2015 | Tsuchiya | A61B 6/4233 |
| 9,148,940 B2* | 9/2015 | Hawver | G01N 23/04 |
| 9,295,146 B2* | 3/2016 | Newman | A61B 6/4233 |
| 9,462,990 B2* | 10/2016 | Kuwabara | A61B 6/54 |
| 9,474,499 B2* | 10/2016 | Exelmans | A61B 6/467 |
| 9,788,809 B2* | 10/2017 | Hiroike | A61B 6/4233 |
| 9,977,135 B2* | 5/2018 | Yokoyama | G01N 23/04 |
| 10,206,647 B2* | 2/2019 | Hiroshige | A61B 6/4233 |
| 2001/0041832 A1* | 11/2001 | Hirai | A61B 6/06 600/407 |
| 2002/0001366 A1* | 1/2002 | Tamura | A61B 6/06 378/155 |
| 2009/0129546 A1* | 5/2009 | Newman | A61B 6/4233 378/114 |
| 2010/0054406 A1* | 3/2010 | Kitano | G01N 23/04 378/62 |
| 2011/0096908 A1* | 4/2011 | Newman | A61B 6/4233 378/116 |
| 2012/0027180 A1* | 2/2012 | Tsuchiya | A61B 6/4233 378/114 |
| 2012/0082294 A1* | 4/2012 | Virshup | A61B 6/405 378/62 |
| 2012/0093295 A1* | 4/2012 | Newman | A61B 6/4233 378/114 |
| 2012/0134474 A1* | 5/2012 | Duca | A61B 6/4233 378/96 |
| 2013/0070896 A1* | 3/2013 | Newman | A61B 6/4233 378/62 |
| 2013/0279661 A1* | 10/2013 | Tamura | H05G 1/56 378/98 |
| 2014/0112446 A1* | 4/2014 | Tsuchiya | A61B 6/4233 378/91 |
| 2014/0146946 A1* | 5/2014 | Newman | A61B 6/4233 378/62 |
| 2014/0169529 A1* | 6/2014 | Hawver | H05G 1/56 378/116 |
| 2014/0211922 A1* | 7/2014 | Kuwabara | A61B 6/54 378/97 |
| 2014/0254760 A1* | 9/2014 | Hiroike | A61B 6/4233 378/62 |
| 2015/0085987 A1* | 3/2015 | Exelmans | A61B 6/467 378/110 |
| 2016/0047920 A1* | 2/2016 | Yokoyama | G01N 23/04 378/62 |
| 2016/0174350 A1* | 6/2016 | Tamura | H05G 1/56 378/114 |
| 2017/0014094 A1* | 1/2017 | Hiroshige | A61B 6/4233 |
| 2017/0292921 A1* | 10/2017 | Ubukata | G01N 23/04 |
| 2018/0000442 A1* | 1/2018 | Hiroike | A61B 6/4233 |
| 2018/0231672 A1* | 8/2018 | Yokoyama | G01N 23/04 |

* cited by examiner

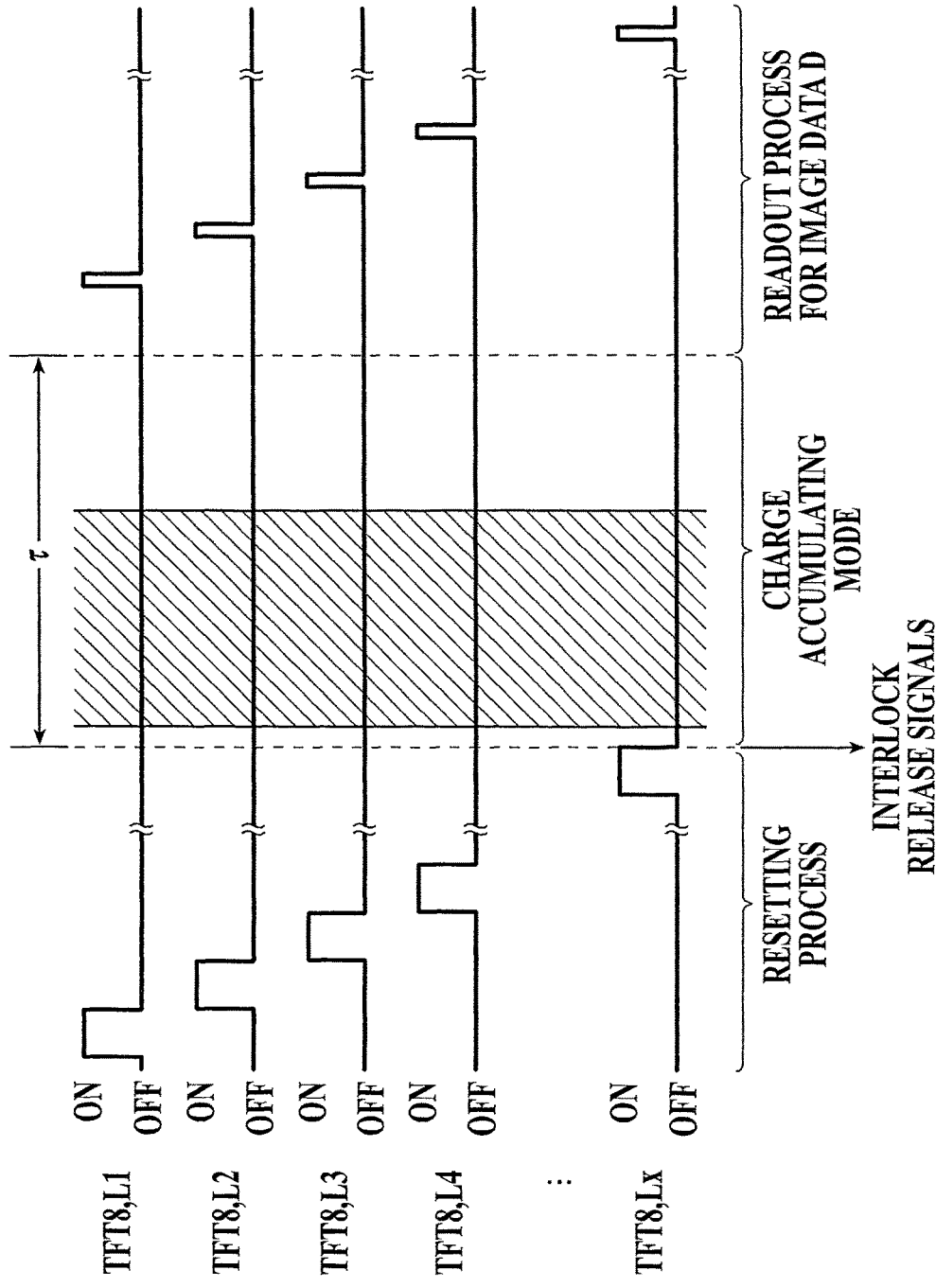

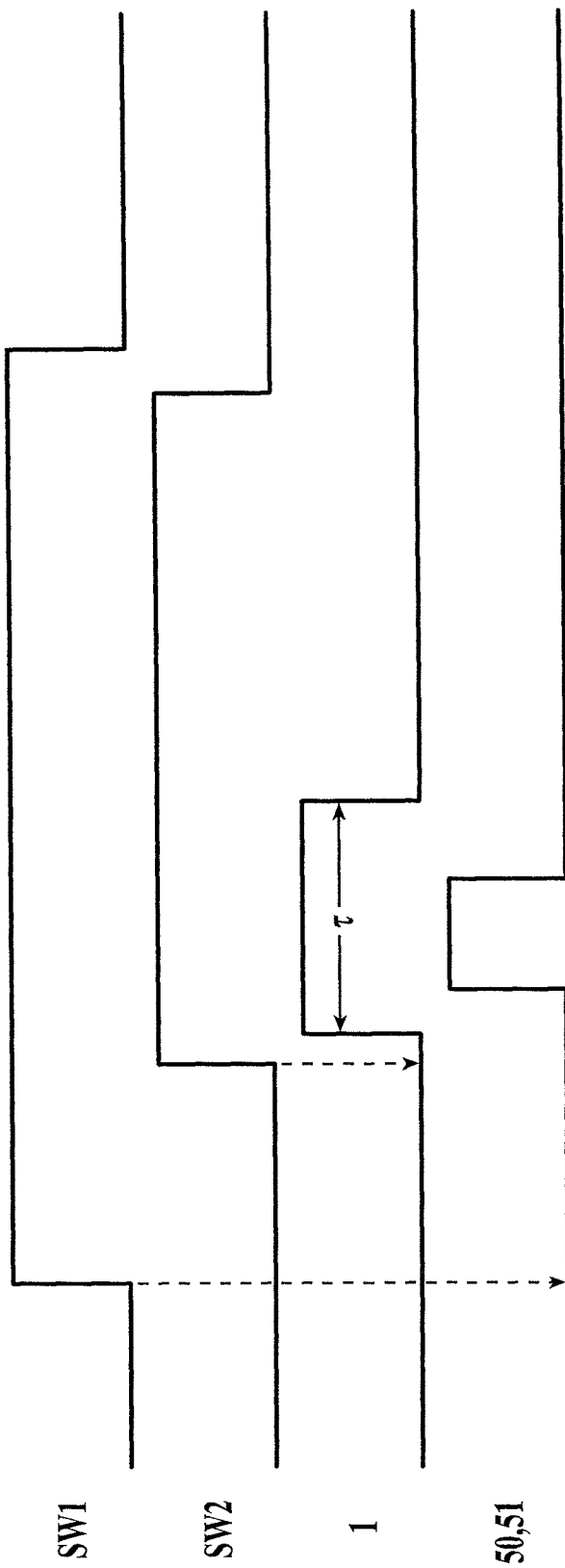

RADIOGRAPHIC IMAGE CAPTURING SYSTEM

CROSS-REFERENCE TO RELATED APPLICATIONS

This application is based upon and claims the benefit of priority from the prior Japanese Patent Application No. 2016-077892 filed on Apr. 8, 2016, the entire contents of which are incorporated herein by reference.

BACKGROUND OF THE INVENTION

Field of the Invention

The present invention relates to a radiographic image capturing system, in specific, a radiographic image capturing system that captures images through irradiation of a radiographic image capturing apparatus with radiation from a radiation irradiating apparatus.

Description of Related Art

Traditional radiographic image capturing systems include radiographic image capturing apparatuses (flat panel detectors (FPD)) to capture radiographic images. In such a radiographic image capturing apparatus, electric charges are generated in individual radiation detecting elements (corresponding to an element indicated with the reference numeral "7" in FIG. 2 described below) in proportion to the dose of irradiated radiation, and are read in the form of image data.

In some of these systems, the image acquisition involves irradiation of the radiographic image capturing apparatus with radiation from a radiation irradiating apparatus while these apparatuses are cooperating with each other through transmission of signals between the radio graphic image capturing apparatus and a generator of the radiation irradiating apparatus.

With reference to FIG. 7, a typical traditional system 100A includes a repeater 40 connected to a generator 51 of a radiation irradiating apparatus 50 and a console 60. The repeater 40 is in wireless communication with a radiographic image capturing apparatus 1 via an access point 41. Alternatively, the repeater 40 may be connected to the radiographic image capturing apparatus 1 with a cable, for example, to establish wire communication therebetween.

With reference to FIG. 8, the radiographic image capturing apparatus 1 resets radiation detecting elements 7 before image acquisition through a resetting process that involves sequentially (or simultaneously) applying on-stage voltages to scanning lines 5(L1) to 5(Lx) from a gate driver 15B (see FIG. 2 described below), to put switching elements 8 connected to the respective radiation detecting elements 7 into the on-state. This process removes the remaining electric charges from the radiation detecting elements 7.

In response to manipulation of a radiologist to an exposure switch 53 connected to an operator station 52 of the radiation irradiating apparatus 50, the generator 51 of the radiation irradiating apparatus 50 transmits radiation start signals via the repeater 40 to the radiographic image capturing apparatus 1. When receiving the radiation start signals, the radiographic image capturing apparatus 1 halts the resetting process for the radiation detecting elements 7, and then applies off-stage voltages from the gate driver 15B to the scanning lines 5(L1) to 5(Lx) to put all the switching elements 8 into the off-state. The radiographic image capturing apparatus 1 thus shifts to a charge accumulating mode where the electric charges generated in the radiation detecting elements 7 are accumulated therein. The radiographic image capturing apparatus 1 then transmits interlock release signals to the generator 51 of the radiation irradiating apparatus 50.

When receiving the interlock release signals, the generator 51 of the radiation irradiating apparatus 50 initiates the irradiation of the radiographic image capturing apparatus 1 with radiation from the radiation irradiating apparatus 50. In FIG. 8, the shaded portion represents the period of irradiation of the radiographic image capturing apparatus 1. After elapse of a predetermined time $\tau$ (hereinafter referred to as "accumulation time $\tau$") from the shift to the charge accumulating mode, the radiographic image capturing apparatus 1 executes a readout process for reading image data D. The readout process involves sequentially applying on-stage voltages from the gate driver 15B to the scanning lines 5(L1) to 5(Lx) to read the image data D from the radiation detecting elements 7. The traditional system 100A is thus constituted.

Unfortunately, the transmission of signals between the radiographic image capturing apparatus 1 and the generator 51 of the radiation irradiating apparatus 50 is sometimes unavailable, for example, if the radiographic image capturing apparatus 1 and the radiation irradiating apparatus 50 are produced by different manufacturers. To solve this problem, the system can be modified as illustrated in FIG. 3 (described below), for example. In detail, the exposure switch 53 of the radiation irradiating apparatus 50 is disconnected from the operator station 52 and connected to the repeater 40, whereas the repeater 40 is disconnected from the generator 51 and connected to the operator station 52. In other words, the repeater 40 is interposed between the operator station 52 of the radiation irradiating apparatus 50 and the exposure switch 53.

In this configuration, in response to manipulation of the radiologist to the exposure switch 53, the repeater 40 transmits the radiation start signals to the radiographic image capturing apparatus 1. The repeater 40 then receives the interlock release signals from the radiographic image capturing apparatus 1, and transfers the interlock release signals to the generator 51 of the radiation irradiating apparatus 50 via the operator station 52. The repeater 40 can thus mediate the transmission of signals between the radiographic image capturing apparatus 1 and the generator 51 of the radiation irradiating apparatus 50 to achieve proper image acquisition, without direct transmission of signals between the radiographic image capturing apparatus 1 and the generator 51 of the radiation irradiating apparatus 50.

The exposure switch 53 of the radiation irradiating apparatus 50 has a structure illustrated in FIG. 9A, for example. In detail, the exposure switch 53 has a first button SW1 and a second button SW2 that can be pressed down independently from each other. In the traditional system 100A illustrated in FIG. 7, if the radiologist performs a first-step manipulation (halfway pressing operation) to the exposure switch 53 by pressing down the first button SW1 as illustrated in FIG. 9B, the exposure switch 53 transmits activation signals to the generator 51 of the radiation irradiating apparatus 50. When receiving the activation signals, the generator 51 activates the radiation irradiating apparatus 50 by, for example, starting the rotation of a rotor (also called a rotary anode; not shown) in the radiation irradiating apparatus 50.

If the radiologist performs a second-step manipulation (all-the-way pressing operation) to the exposure switch 53 by pressing down the first button SW1 and the second button SW2 as illustrated in FIG. 9C, the exposure switch 53 transmits the radiation start signals to the generator 51 of the radiation irradiating apparatus 50. The generator 51 then transfers the radiation start signals to the radiographic image capturing apparatus 1 as described above. When receiving the interlock release signals from the radiographic image capturing apparatus 1, the generator 51 initiates the radiation emission from the radiation irradiating apparatus 50.

In general, the radiation irradiating apparatus 50 requires approximately one second from start of the rotation of the rotor to stable radiation emission (e.g., to the constant rotation of the rotor), although the time may vary depending on the radiation irradiating apparatus 50. Many radiologists thus perform the first-step manipulation to the exposure switch 53, wait for approximately one second, and then perform the second-step manipulation. Some radiologi+sts simultaneously perform the first-step and second-step manipulations (by a single movement). In response to the simultaneous manipulations, the generator 51 transmits the radiation start signals to the radiographic image capturing apparatus 1 after the stabilization of the rotor in the radiation irradiating apparatus 50. It also takes approximately one second from the manipulations of the exposure switch 53 to the start of radiation emission.

In a radiographic image capturing system 100 illustrated in FIG. 3 (described below), when the exposure switch 53 transmits the activation signals in response to the first-step manipulation of the exposure switch 53 by pressing down the first button SW1 (see FIG. 9B) as illustrated in FIG. 10, the repeater 40 transfers the activation signals via the operator station 52 to the generator 51 of the radiation irradiating apparatus 50. When receiving the activation signals, the generator 51 activates the radiation irradiating apparatus 50 by, for example, initiating the rotation of the rotor.

With reference to FIG. 10, when the radiologist performs the second-step manipulation of the exposure switch 53 by pressing down also the second button SW2 after elapse of approximately one second from the first-step manipulation by pressing down the first button SW1, the exposure switch 53 transmits the radiation start signals. The repeater 40 then transfers the radiation start signals to the generator 51 of the radiation irradiating apparatus 50 and the radiographic image capturing apparatus 1.

The radiographic image capturing apparatus 1 shifts to the charge accumulating mode and transmits the interlock release signals. At this time, the rotation of the rotor has already been stabilized in the radiation irradiating apparatus 50. The generator 51 of the radiation irradiating apparatus 50 thus initiates the radiation emission from the radiation irradiating apparatus 50 immediately after receiving the interlock release signals from the radiographic image capturing apparatus 1 via the repeater 40.

In this case, the irradiation of the radiographic image capturing apparatus 1 from the radiation irradiating apparatus 50 can be conducted during the charge accumulating mode of the radiographic image capturing apparatus 1 (i.e., during the accumulation time τ), as illustrated in FIG. 10. FIG. 10 (and FIG. 11 to be described later, etc.) is a time chart illustrating the on/off-states of the first and second buttons SW1 and SW2, the mode of the radiographic image capturing apparatus 1 (the period of the raised line corresponds to the charge accumulating mode), and the emission/non-emission of radiation from the radiation irradiating apparatus 50.

In contrast, with reference to FIG. 11, the radiologist may simultaneously or substantially simultaneously press down the first and second buttons SW1 and SW2 of the exposure switch 53 in the radiographic image capturing system 100 illustrated in FIG. 3 in some cases. In such cases, the exposure switch 53 transmits both the activation and radiation start signals. The repeater 40 transfers the activation and radiation start signals to the generator 51 of the radiation irradiating apparatus 50, and the radiation start signals to the radiographic image capturing apparatus 1.

The radiographic image capturing apparatus 1 then immediately halts the resetting process for the radiation detecting elements 7 to shift to the charge accumulating mode, and transmits the interlock release signals. The generator 51 of the radiation irradiating apparatus 50 activates the radiation irradiating apparatus 50 when receiving the activation and radiation start signals from the repeater 40. Approximately one second later, the rotation of the rotor in the radiation irradiating apparatus 50 is stabilized. At this time, the generator 51 of the radiation irradiating apparatus 50 has already received the interlock release signals from the radiographic image capturing apparatus 1 and thus initiates the radiation emission from the radiation irradiating apparatus 50.

At the start of emission, the accumulation time τ has almost elapsed from the shift of the radiographic image capturing apparatus 1 to the charge accumulating mode. Unfortunately, with reference to the second chart from the bottom of FIG. 11, the radiographic image capturing apparatus 1 may terminate the charge accumulating mode and initiate the readout process for the image data D in the middle of the radiation emission from the radiation irradiating apparatus 50. In this case, the radiographic image acquired at the radiographic image capturing apparatus 1 may have low image quality due to an insufficient dose of radiation to the radiographic image capturing apparatus 1.

In another case illustrated in the bottom chart of FIG. 11, the radiographic image capturing apparatus 1 may have already terminated the charge accumulating mode and initiated the readout process for the image data D at the start of radiation emission from the radiation irradiating apparatus 50. In this case, the radiographic image acquired at the radiographic image capturing apparatus 1 cannot capture the subject at all and needs reacquisition.

To solve this problem, the accumulation time τ (i.e., the period of the charge accumulating mode) in the radiographic image capturing apparatus 1 can be prolonged, for example. Unfortunately, as the accumulation time τ increases, the radiographic image capturing apparatus 1 becomes more ready to pick up noise. The noise adversely affects the read image data D and decreases the quality of the acquired radiographic image.

To avoid such a decrease in image quality, a typical traditional system further includes an x-ray sensor installed in the radiographic image capturing apparatus 1, or disposed in the range of radiation emission from the radiation irradiating apparatus 50 and connected to the console 60 and the repeater 40. In this configuration, the radiologist manipulates the exposure switch 53 to cause radiation emission from the radiation irradiating apparatus 50. On the basis of the output from the x-ray sensor, any one of the radiographic image capturing apparatus 1, the console 60, and the repeater 40 measures the time (hereinafter referred to as "delay time") from the simultaneous manipulations of the radiologist to the first and second buttons SW1 and SW2 of the exposure switch 53 to the actual start of radiation emission from the radiation irradiating apparatus 50. The delay time is measured and stored for each radiation irradiating apparatus 50 in advance.

Before the image acquisition, the radiographic image capturing apparatus 1 is adjusted based on the delay time such that the timing of shift to the charge accumulating mode is delayed from the timing of manipulations of the exposure switch 53 by the radiologist as required. The radiation irradiating apparatus 50 can thus emit radiation during the charge accumulating mode of the radiographic image capturing apparatus 1.

A system disclosed in Japanese Patent Application Laid-Open Publication No. 2012-29920 determines the delay time before the image acquisition. The determining procedure involves repeating the readout processes for reading image data D at a radiographic image capturing apparatus 1, generating radiographic images based on the respective pieces of read image data D, and analyzing the generated radiographic images.

Unfortunately, the procedure of measuring the delay time with the x-ray sensor requires many man-hours for preparation of the x-ray sensor, and installation of the x-ray sensor in the radiographic image capturing apparatus 1, or connection of the x-ray sensor to the console 60 and the repeater 40 and placement of the x-ray sensor in the range of radiation emission from the radiation irradiating apparatus 50, for example. This procedure thus cannot effectively determine the delay time. The procedure of determining the delay time disclosed in Japanese Patent Application Laid-Open Publication No. 2012-29920 requires extra preliminary operation of repeating the readout processes for image data D at the radiographic image capturing apparatus 1.

SUMMARY OF THE INVENTION

An object of the present invention, which has been accomplished to solve the above problems, is to provide a radiographic image capturing system that can determine the delay time in a radiation irradiating apparatus by a simple procedure.

To achieve the above object, a radiographic image capturing system in which one aspect of the present invention is reflected includes: a radiation irradiating apparatus which emits radiation and provides notification of radiation emission while emitting the radiation; a radiographic image capturing apparatus which includes a plurality of radiation detecting elements disposed in a two-dimensional matrix and executes an image data reading process to read one or more electric charges accumulated in the respective radiation detecting elements as image data; an exposure switch capable of two-step manipulations, the exposure switch transmitting an activation signal in response to a first-step manipulation and transmitting a radiation start signal in response to a second-step manipulation; a signal transceiver which receives the activation signal transmitted from the exposure switch and transfers the received activation signal to the radiation irradiating apparatus; and a delay time calculating device which calculates, as a delay time, a difference between a time of reception of the activation signal from the exposure switch at the signal transceiver and a time of start of the notification of radiation emission at the radiation irradiating apparatus.

A radiographic image capturing system in which another aspect of the present invention is reflected includes: a radiation irradiating apparatus which emits radiation; a radiographic image capturing apparatus which includes a plurality of radiation detecting elements disposed in a two-dimensional matrix, executes an image data reading process to read one or more electric charges accumulated in the respective radiation detecting elements as image data, and has a function capable of autonomously detecting start of radiation emission from the radiation irradiating apparatus; an exposure switch which transmits an activation signal to make the radiation irradiating apparatus activated; a signal transceiver which receives the activation signal transmitted from the exposure switch and transfers the received activation signal or transfers a new activation signal upon reception of the activation signal; and a delay time calculating device which calculate a delay time as a difference between a time of reception of the activation signal from the exposure switch at the signal transceiver and a time of detection of the start of radiation emission from the radiation irradiating apparatus at the radiographic image capturing apparatus, wherein the delay time calculating device stores a preliminarily calculated delay time or a preset delay time as a first delay time in a storage device; calculates, as a second delay time, the delay time which is the difference between the time of reception of the activation signal from the exposure switch at the signal transceiver and the time of detection of the start of radiation emission from the radiation irradiating apparatus at the radiographic image capturing apparatus during image capture; and updates the first delay time stored in the storage device with the second delay time and/or provides a notification to a user if an absolute value of a difference between the calculated second delay time and the first delay time stored in the storage device becomes equal to or larger than a predetermined threshold.

BRIEF DESCRIPTION OF THE DRAWINGS

The present invention will become more fully understood from the detailed description given hereinbelow and the appended drawings, and thus are not intended as a definition of the limits of the present invention, and wherein:

FIG. 8 is a time chart illustrating the timings of sequential application of on-stage voltages to individual TFTs in a resetting process, a shift to a charge accumulating mode and a readout process for image data of radiation detecting elements in a radiographic image capturing apparatus, etc.;

FIG. 10 illustrates the relation between a charge accumulating mode and the period of radiation emission in the case of pressing of first and second buttons of the exposure switch with a time interval in the radiographic image capturing system in FIG. 3, without the process according to the embodiment.

PREFERRED EMBODIMENT OF THE PRESENT INVENTION

Embodiments of the radiographic image capturing system of the present invention will now be described with reference to the accompanying drawings.

The following description focuses on an example system provided with a portable radiographic image capturing apparatus including a housing 2 (see FIG. 1 described below) accommodating a sensor substrate (not shown) having a plurality of radiation detecting elements 7 (see FIG. 2 described below) disposed in a two dimensional matrix. This example should not be construed to limit the present invention. The radiographic image capturing apparatus may also be of a dedicated (fixed) type including a sensor substrate integrated with a support base, for example.

[Configuration of Radiographic Image Capturing Apparatus]

Figure 1:
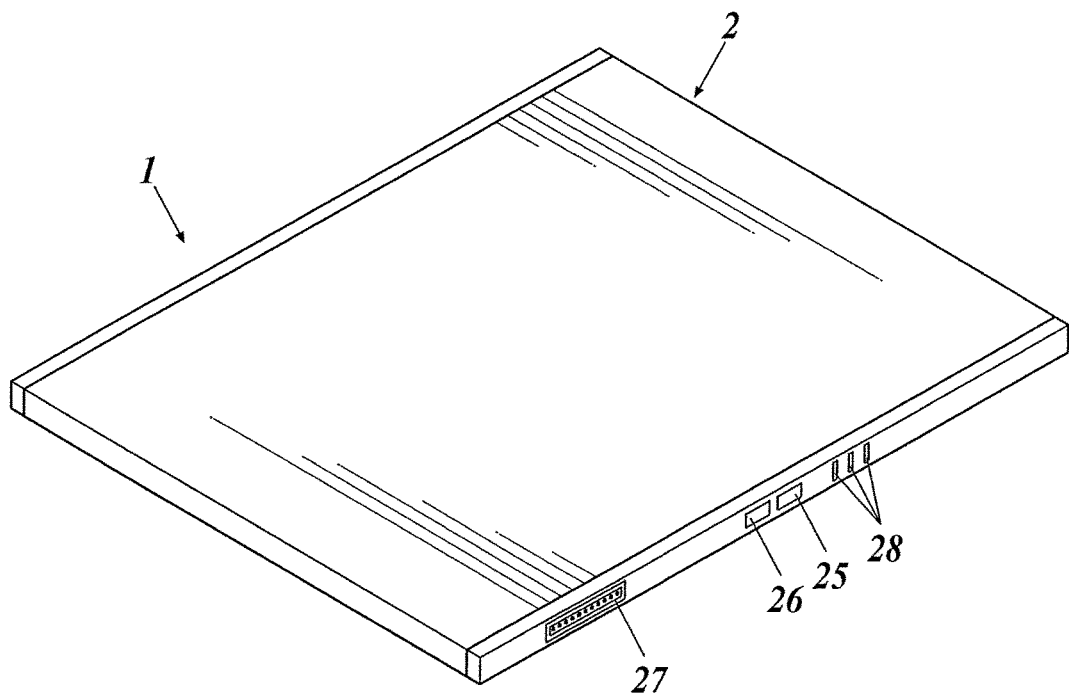
FIG. 1 is a perspective view of a radiographic image capturing apparatus.
Figure 2:
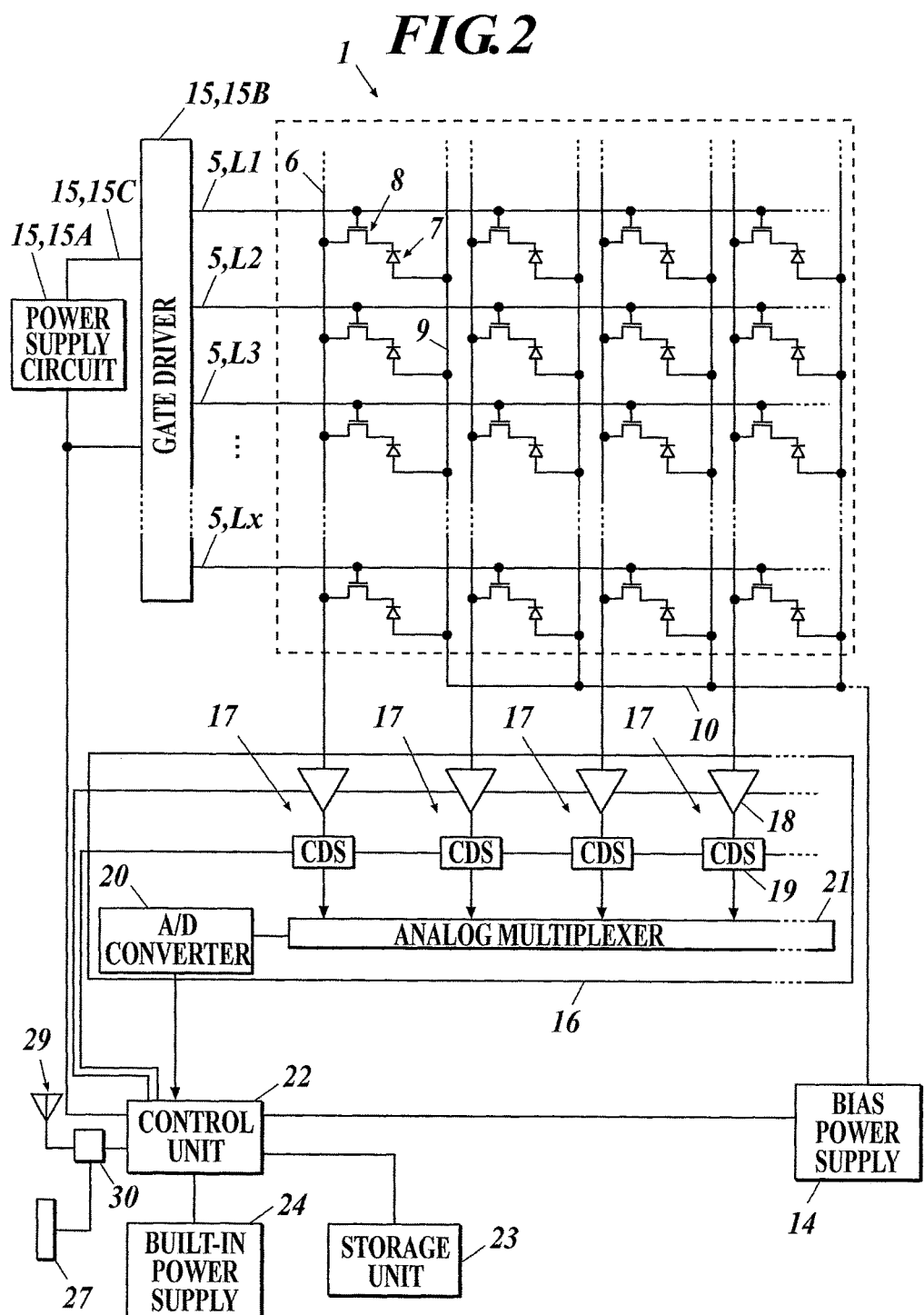
FIG. 2 is a block diagram illustrating an equivalent circuit of the radiographic image capturing apparatus.

The configuration of the radiographic image capturing apparatus will now be described. FIG. 1 is a perspective view of the radiographic image capturing apparatus. FIG. 2 is a block diagram illustrating an equivalent circuit of the radiographic image capturing apparatus. A radiographic image capturing apparatus 1 has the two-dimensional matrix of radiation detecting elements 7 (see FIG. 2) disposed on the sensor substrate (not shown) in the housing 2 (see FIG. 1).

With reference to FIG. 1, the radiographic image capturing apparatus 1 includes a power switch 25, a toggle switch 26, a connector 27, and an indicator 28 which are disposed on one side of the housing 2. The housing 2 is provided with an antenna 29 (see FIG. 2, which will described below) on, for example, the opposite side (not shown) of the housing 2 for wireless communications with an external device.

As shown in FIG. 2, radiation detecting elements 7 are connected to bias lines 9. A bias power supply 14 applies a reverse bias voltage via the bias lines 9 and their connections 10 to the radiation detecting elements 7. The radiation detecting elements 7 are also connected to the respective thin film transistors (TFTs) 8, which function as switching elements. Each TFT 8 is connected to the corresponding signal line 6. The radiation detecting element 7 generates electric charges in proportion to the dose of the received radiation.

In a scan driving unit 15, on-stage voltage or off-state voltage is applied from a power supply circuit 15A to a gate driver 15B via a line 15C and then distributed to scanning lines 5(L1) to 5(Lx). The off-state voltage applied to each TFT 8 via the corresponding scanning line 5 puts the TFT 8 into the off-state, resulting in disconnection between the corresponding radiation detecting element 7 and the corresponding signal line 6 to accumulate electric charge in the radiation detecting element 7. In contrast, the on-state voltage applied to each TFT 8 via the corresponding scanning line 5 puts the TFT 8 into the on-state, resulting in the release of the electric charge accumulated in the corresponding radiation detecting element 7 to the corresponding signal line 6.

Each signal line 6 is connected to the corresponding readout circuit 17 in a readout IC 16. In order to read image data D, the gate driver 15B sequentially applies the on-stage voltage to the scanning lines 5(L1) to 5(Lx). The on-stage voltage applied puts the TFTs 8 into the on-state, which causes the electric charges to flow from the radiation detecting elements 7 into the readout circuits 17 via the TFTs 8 and the signal lines 6. Each amplifying circuit 18 outputs a voltage value in proportion to the electric charge received.

Correlated double sampling circuits 19 (CDSs in FIG. 2) each read the voltage value output from the corresponding amplifying circuit 18 as an analog image data D and sequentially send the analog image data D to an A/D converter 20 via an analog multiplexer 21. The analog image data D are sequentially converted into digital image data D at the A/D converter 20 and the digital image data are sequentially stored in a storage unit 23.

A control unit 22 may be a computer provided with a not-shown central processing unit (CPU), read only memory (ROM), random access memory (RAM) and input/output interface, each being connected to a bus. Alternatively, the control unit 22 may be a field programmable gate array (FPGA). Alternatively, the control unit 22 may include a dedicated control circuit.

The control unit 22 is connected to the storage unit 23, a built-in power supply 24, and a communication device 30. The storage unit 23 includes a static RAM (SRAM), synchronous DRAM (SDRAM), or NAND flash memory. The built-in power supply 24 includes a lithium ion capacitor. The communication device 30 is configured to communicate with an external device through a wireless or wired network via the antenna 29 or connector 27.

With reference to FIG. 8, the control unit 22 controls the scan driving unit 15 to execute a resetting process for resetting the radiation detecting elements 7, controls the gate driver 15B of the scan driving unit 15 to apply off-stage voltages to the individual TFTs 8 through the scanning lines 5(L1) to 5(Lx) such that the radiographic image capturing apparatus 1 shifts to a charge accumulating mode, and controls the scan driving unit 15 and the readout circuits 17 to execute a readout process for reading the image data D from the radiation detecting elements 7. The control unit 22 also controls the storage of the read image data D into the storage unit 23 and the transmission of the image data D to an external device via the communication unit 30.

[Radiographic Image Capturing System]

Figure 3:
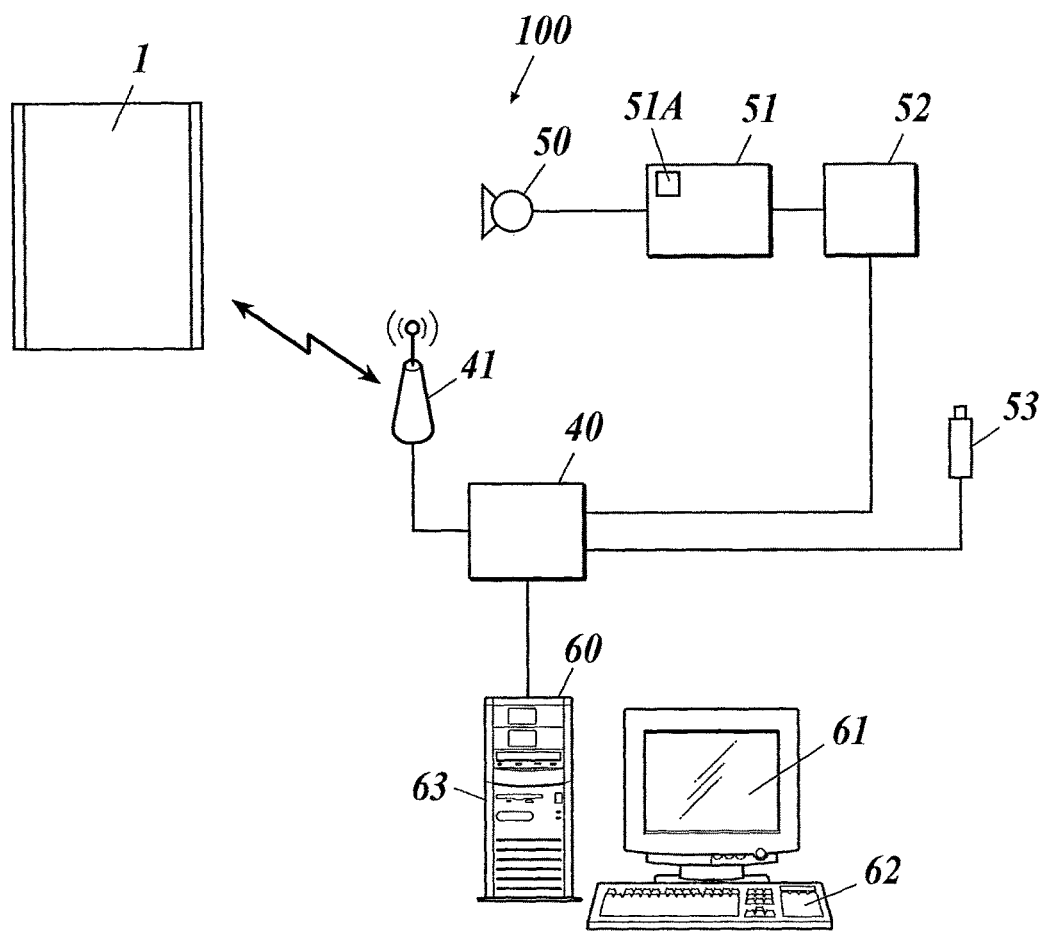
FIG. 3 illustrates an example configuration of a radiographic image capturing system according to an embodiment of the present invention.

A radiographic image capturing system 100 according to an embodiment will now be described. With reference to FIG. 3, the radiographic image capturing system 100 includes the radiographic image capturing apparatus 1, a repeater 40 (a signal transceiver), a radiation irradiating apparatus 50, and a console 60. In the embodiment, the repeater 40 is connected to an operator station 52 of the radiation irradiating apparatus 50. The repeater 40 can thus transmit signals to a generator 51 of the radiation irradiating apparatus 50 via the operator station 52.

In the embodiment, the repeater 40 is also connected to an exposure switch 53 of the radiation irradiating apparatus 50. The exposure switch 53 is capable of two-step manipulations. In response to a first-step manipulation of pressing down the first button SW1 (halfway pressing operation; see FIG. 9B) by a radiologist, the exposure switch 53 transmits activation signals. In response to a second-step manipulation of pressing down the first button SW1 and the second button SW2 (all-the-way pressing operation; see FIG. 9C) by the radiologist, the exposure switch 53 transmits radiation start signals.

The repeater 40 receives the activation and radiation start signals from the exposure switch 53. The repeater 40 is also connected to the console 60 and is in wireless communication with the radiographic image capturing apparatus 1 via an access point 41. Alternatively, the repeater 40 may be connected to the radiographic image capturing apparatus 1 with a cable, for example, to establish wire communication therebetween.

Figure 4:
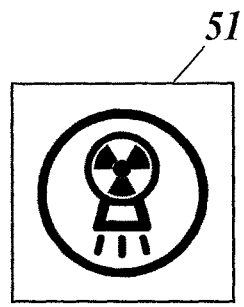
FIG. 4 illustrates an example figure displayed by illumination at a notifying unit of a generator of a radiation irradiating apparatus.

In the embodiment, the generator 51 of the radiation irradiating apparatus 50 activates the radiation irradiating apparatus 50 when receiving the activation signals, and initiates the radiation emission from the radiation irradiating apparatus 50 when receiving interlock release signals. The generator 51 includes a notifying unit 51A, such as a buzzer. During the radiation emission from the radiation irradiating apparatus 50, the notifying unit 51A notifies the radiologist of the ongoing emission by, for example, generating buzzer sound or displaying a predetermined figure illustrated in FIG. 4 by illumination.

The notifying unit 51A may also use any other notification method, such as vibration, other than the sound and illumination. In the embodiment, the notifying unit 51A provides the notification of radiation emission with sound, illumination, and vibration alone or any combination thereof. The notifying unit 51A can thus certainly notifies the radiologist of the ongoing radiation emission from the radiation irradiating apparatus 50.

The notifying unit 51A may be provided to the generator 51 of the radiation irradiating apparatus 50 as illustrated in FIG. 3, or provided to the operator station 52 of the radiation irradiating apparatus 50. Alternatively, the generator 51 and the operator station 52 may each include the notifying unit 51A.

The console 60 includes a computer provided with a not-shown central processing unit (CPU), read only memory (ROM), random access memory (RAM), and input/output interface, which are connected to each other with buses. The console 60 may be a dedicated apparatus.

The console 60 is connected to a display unit 61 including a cathode ray tube (CRT) display or liquid crystal display (LCD), and to an input unit 62, such as a mouse, keyboard, and/or touch panel. The console 60 is provided with a storage unit 63 connected thereto or installed therein and including a hard disk drive (HDD).

[Calculation of Delay Time]

The calculation of a delay time $\Delta T$ in the radiographic image capturing system 100 will now be explained according to the embodiment. The calculation of the delay time $\Delta T$ is executed, for example, at the time of installation of the radiation irradiating apparatus 50 into a hospital or at the time of maintenance of the radiographic image capturing system 100.

Although the console 60 functions as a delay time calculating device for calculating the delay time $\Delta T$ in the embodiment, the delay time $\Delta T$ may also be calculated at the control unit 22 of the radiographic image apparatus 1 or a microcomputer (not shown) installed in the repeater 40. The explanation below also holds true for the latter case.

Figure 5:
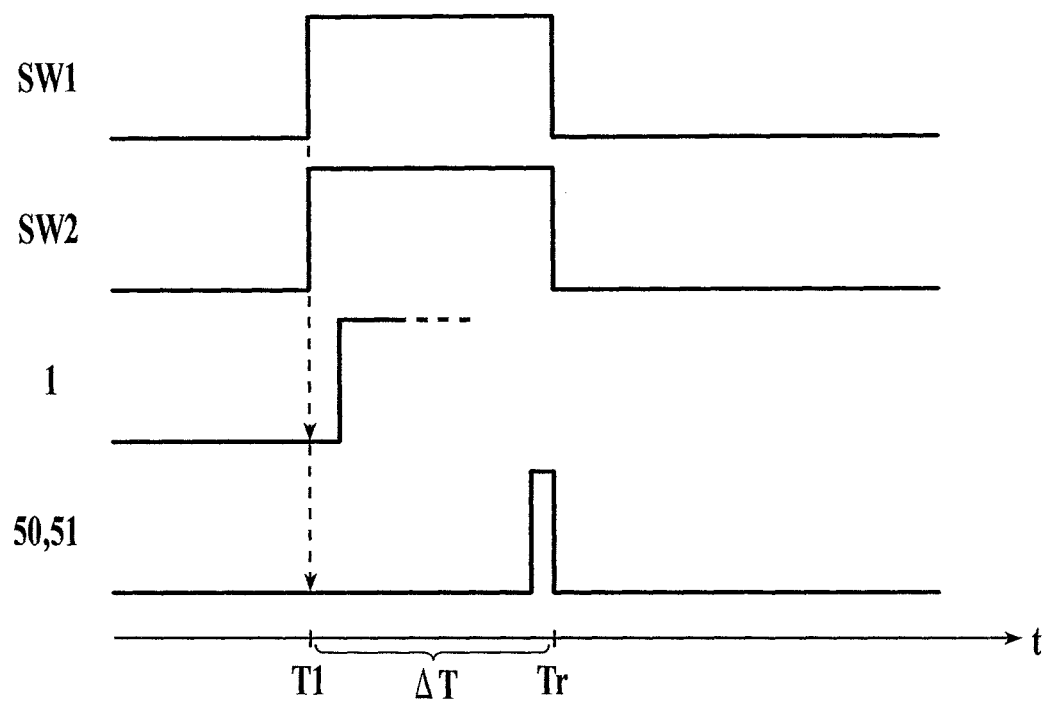
FIG. 5 illustrates a procedure of calculating a delay time and the calculated delay time according to the embodiment.

FIG. 5 illustrates the calculation of the delay time $\Delta T$ according to the embodiment. First, when the radiologist simultaneously presses down the first and second buttons SW1 and SW2 of the exposure switch 53 (i.e., turns the exposure switch 53 from the mode in FIG. 9A to the all-the-way pressed mode in FIG. 9C), the exposure switch 53 transmits the activation and radiation start signals.

When receiving the activation and radiation start signals from the exposure switch 53, the repeater 40 immediately transfers the received activation and radiation start signals to the generator 51 of the radiation irradiating apparatus 50 via the operator station 52, and the received radiation start signal to the radiographic image capturing apparatus 1. The repeater 40 also transmits information on the time of reception of the activation signal from the exposure switch 53 at the repeater 40, to the console 60.

When receiving the activation signal from the repeater 40, the generator 51 of the radiation irradiating apparatus 50 activates the radiation irradiating apparatus 50 by, for example, starting the rotation of a rotor in the radiation irradiating apparatus 50. When receiving the radiation start signal from the repeater 40, the radiographic image capturing apparatus 1 halts the resetting process for the radiation detecting elements 7 to shift to the charge accumulating mode, as illustrated in FIG. 8, and transmits an interlock release signal. When receiving the interlock release signal from the radiographic image capturing apparatus 1, the repeater 40 transfers the received signal to the generator 51 of the radiation irradiating apparatus 50.

In this case, the radiographic image capturing apparatus 1 does not have to execute the processes (i.e., the continuation of the charge accumulating mode and the readout process for the image data D) subsequent to the transmission of the interlock release signal. In the embodiment, the console 60 receives the information on the time of reception of the activation signal from the exposure switch 53 at the repeater 40, from the repeater 40, and then records the time as a time T1 at which the repeater 40 receives the activation signal from the exposure switch 53.

The generator 51 of the radiation irradiating apparatus 50 has already received the interlock release signal in this case. Thus, after stabilizing the radiation emission (e.g., achieving the constant rotation of the rotor), the generator 51 initiates the radiation emission from the radiation irradiating apparatus 50. The generator 51 also controls the notifying unit 51A (see FIG. 3) to initiate the notification of radiation emission from the radiation irradiating apparatus 50 with the buzzer sound or illumination.

Figure 9A:
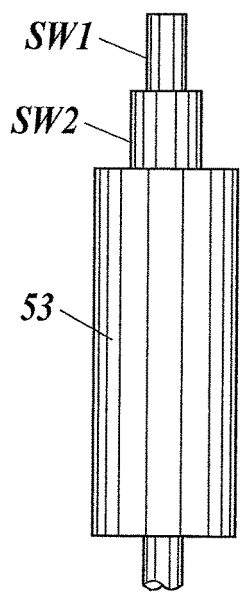
FIG. 9A illustrates an exposure switch.
Figure 9B:
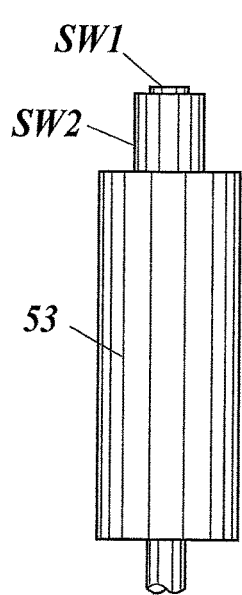
FIG. 9B illustrates the exposure switch in a halfway pressed mode.
Figure 9C:
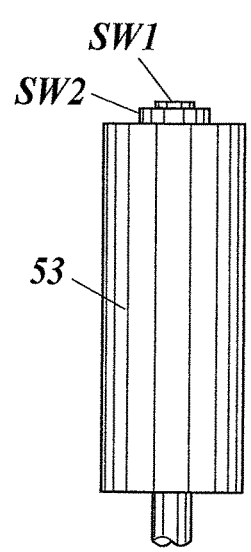
FIG. 9C illustrates the exposure switch after all-the-way pressed mode.

With reference to FIG. 5, immediately after the start of the notification at the notifying unit 51A of the generator 51, the radiologist releases the first and second buttons SW1 and SW2 of the exposure switch 53 (i.e., returns the exposure switch 53 from the all-the-way pressed mode in FIG. 9C to the mode in FIG. 9A). At that time, the radiation irradiating apparatus 50 halts the radiation emission accompanied by the termination of the notification at the notifying unit 51A. The generator 51 of the radiation irradiating apparatus 50 then transmits a termination signal indicating the halt of the radiation emission from the radiation irradiating apparatus 50.

The console 60 receives the termination signal via the repeater 40 and then records the time of reception of the termination signal by the console 60 as a time Tr of the start of the notification of radiation emission at the notifying unit 51A of the generator 51 of the radiation irradiating apparatus 50. Alternatively, if the repeater 40 transmits to the console 60 information on the time of reception of the termination signal by the repeater 40, the console 60 records the time according to the received information as the time Tr. The time of the start of the notification of radiation emission at the notifying unit 51A of the generator 51 of the radiation irradiating apparatus 50 is substantially contemporary with the time of transmission of the termination signal from the generator 51 of the radiation irradiating apparatus 50.

The console 60 determines the delay time ΔT by calculating the difference between the time T1 (see FIG. 5) and the time Tr according to Expression (1) below, and stores the determined delay time ΔT in the storage unit 63 (see FIG. 3).

$$\Delta T = Tr - T1 \quad (1)$$

In the radiographic image capturing system 100 including multiple radiation irradiating apparatuses 50, the delay times ΔT are calculated for the respective radiation irradiating apparatuses 50. The delay time ΔT can be more accurately determined by, for example, repeating the above calculation multiple times (e.g., three times) and calculating the average of the resulting delay times ΔT.

The radiologist may fail in manipulation of the exposure switch 53 (e.g., press down the first button SW1 but forget to press down the second button SW2), or fail to immediately release the exposure switch 53 after the start of the notification at the notifying unit 51A of the generator 51 of the radiation irradiating apparatus 50 in some cases. In such cases, the calculated delay time ΔT is significantly deviated from the average of the delay times ΔT, and a difference between the calculated delay time ΔT and the average of the delay times ΔT becomes exceptionally longer or shorter. To avoid the adverse effects of such an exceptional delay time ΔT, the calculated delay time ΔT of an unexpected value may be excluded from the calculation of the average, or the display unit 61 (see FIG. 3) of the console 60 may perform an error display.

The calculated average of the delay times ΔT may be longer than a predetermined threshold because of the repetitive determination of exceptional delay times ΔT, which indicates any abnormality in the radiation irradiating apparatus 50. In this case, the display unit 61 of the console 60 may notify the user (e.g., radiologist) of this situation with an error display representing the determination of exceptionally long delay times ΔT or possible abnormality in the radiation irradiating apparatus 50, for example. This configuration can simultaneously achieve the calculation of the delay time ΔT and the detection of abnormality in the radiation irradiating apparatus 50.

The log level in the calculation of delay times ΔT may be varied from the log level in the normal image acquisition in the radiographic image capturing system 100, to more accurately determine the times T1 and Tr, leading to more accurate determination of the delay time ΔT.

Advantageous Effects

As explained above, in the radiographic image capturing system 100 according to the embodiment, the delay time ΔT in the radiation irradiating apparatus 50 or the generator 51 can be calculated by simple manipulations of the radiologist that involve simultaneously pressing down the first and second buttons SW1 and SW2 of the exposure switch 53 and releasing the exposure switch 53 at the time when the notifying unit 51A of the generator 51 of the radiation irradiating apparatus 50 starts the notification of radiation emission by generating the buzzer sound or illumination.

The delay time ΔT in the radiation irradiating apparatus 50 or the generator 51 can thus be determined by a very simple procedure in the embodiment, without many man-hours for preparation of an x-ray sensor, and installation of the x-ray sensor in the radiographic image capturing apparatus 1, or connection of the x-ray sensor to the console 60 and the repeater 40 and placement of the x-ray sensor in the range of radiation emission from the radiation irradiating apparatus 50.

The radiographic image capturing system 100 according to the embodiment may further include, for example, a detecting unit such as an acoustic sensor, a photosensor, or a vibration sensor capable of detecting the buzzer sound, illumination, or vibration, respectively, from the notifying unit 51A of the generator 51 of the radiation irradiating apparatus 50. In this case, the console 60 may calculate the delay time ΔT from the time Tr when the detecting unit detects the notification at the notifying unit 51A (i.e., the time Tr of the start of the notification of radiation emission at the notifying unit 51A of the generator 51 of the radiation irradiating apparatus 50), instead of the time Tr of reception of the termination signal from the generator 51 at the console 60 via the repeater 40.

[Utilization of Delay Time to Image Capturing]

The delay time ΔT (or the average of the delay times ΔT; the same shall apply hereinafter) calculated as described above is applied to the image acquisition, to determine the appropriate timing of shift of the radiographic image capturing apparatus 1 to the charge accumulating mode after the manipulation of the exposure switch 53 of the radiation irradiating apparatus 50 (i.e., to avoid the problems illustrated in FIG. 11). The detail will now be described.

Figure 11:
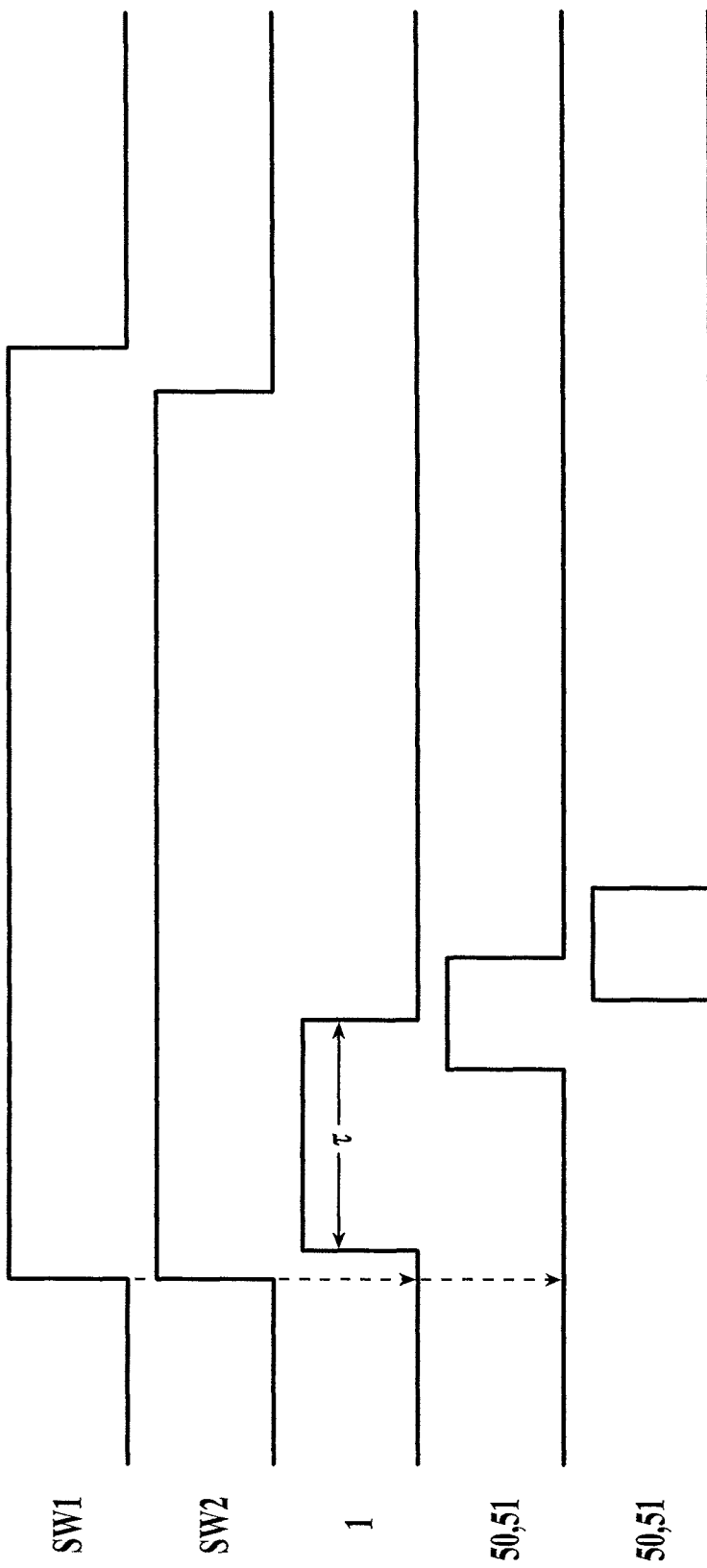
FIG. 11 illustrates the relation between a charge accumulating mode and the period of radiation emission in the case of simultaneous pressing of first and second buttons of the exposure switch in the radiographic image capturing system in FIG. 3, without the process according to the embodiment.

The problems illustrated in FIG. 11 are caused by deviations of the timing of the shift of the radiographic image capturing apparatus 1 to the charge accumulating mode and the timing of the start of radiation emission from the radiation irradiating apparatus 50 from the proper timings illustrated in FIG. 10. These problems can be avoided by adjusting the timing of the shift of the radiographic image capturing apparatus 1 to the charge accumulating mode based on the delay time ΔT.

In detail, for example, the control unit 22 may control the radiographic image capturing apparatus 1 to shift to the charge accumulating mode after elapse of a waiting time Tw from the reception of the radiation start signal at the repeater 40 that are transmitted from the exposure switch 53 in response to the second-step manipulation (all-the-way pressing operation) to the exposure switch 53 in the image acquisition.

Figure 6A:
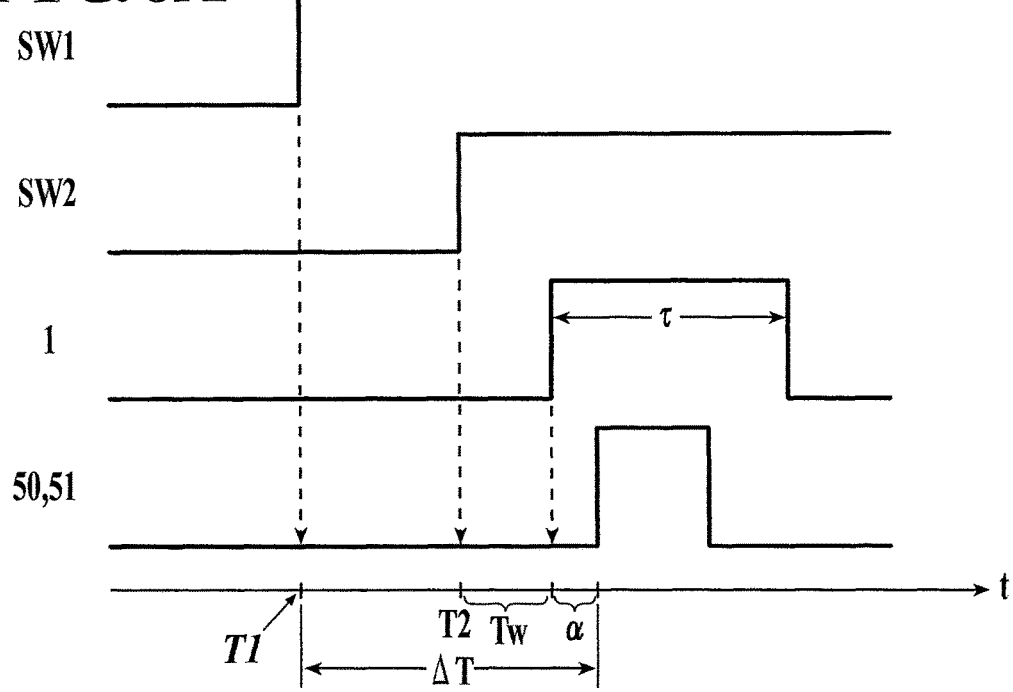
FIG. 6A illustrates the relation among a delay time ΔT, times T1 and T2, and waiting time Tw in the case of pressing of first and second buttons of an exposure switch with a time interval.
Figure 6B:
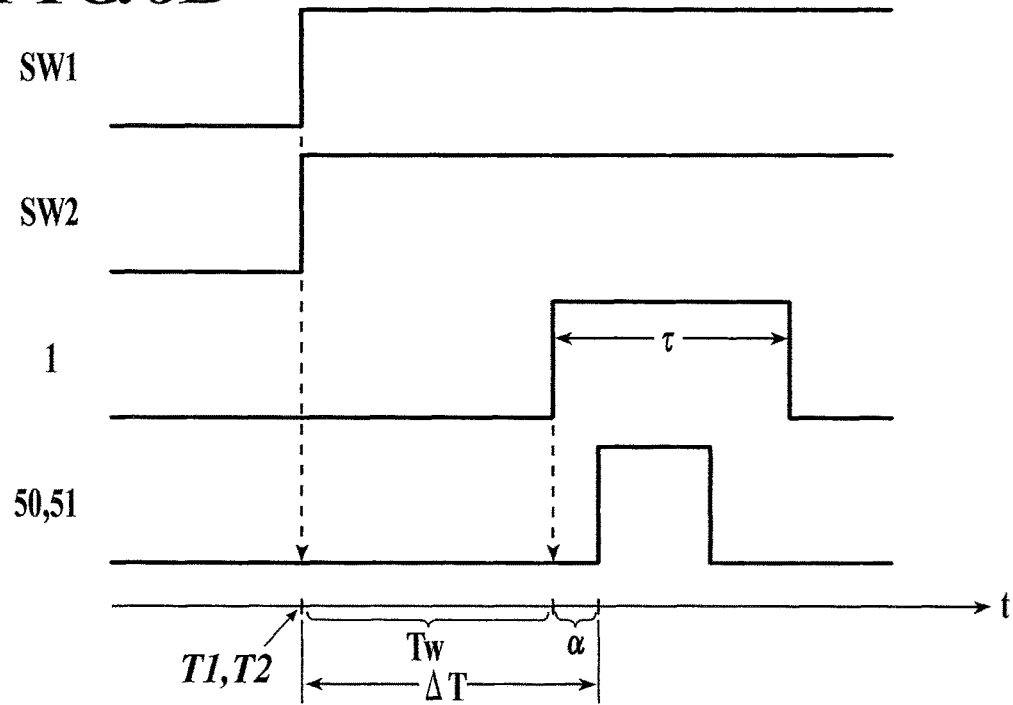
FIG. 6B illustrates the relation among a delay time ΔT, times T1 and T2, and waiting time Tw in the case of simultaneous pressing of first and second buttons of an exposure switch.
Figure 7:
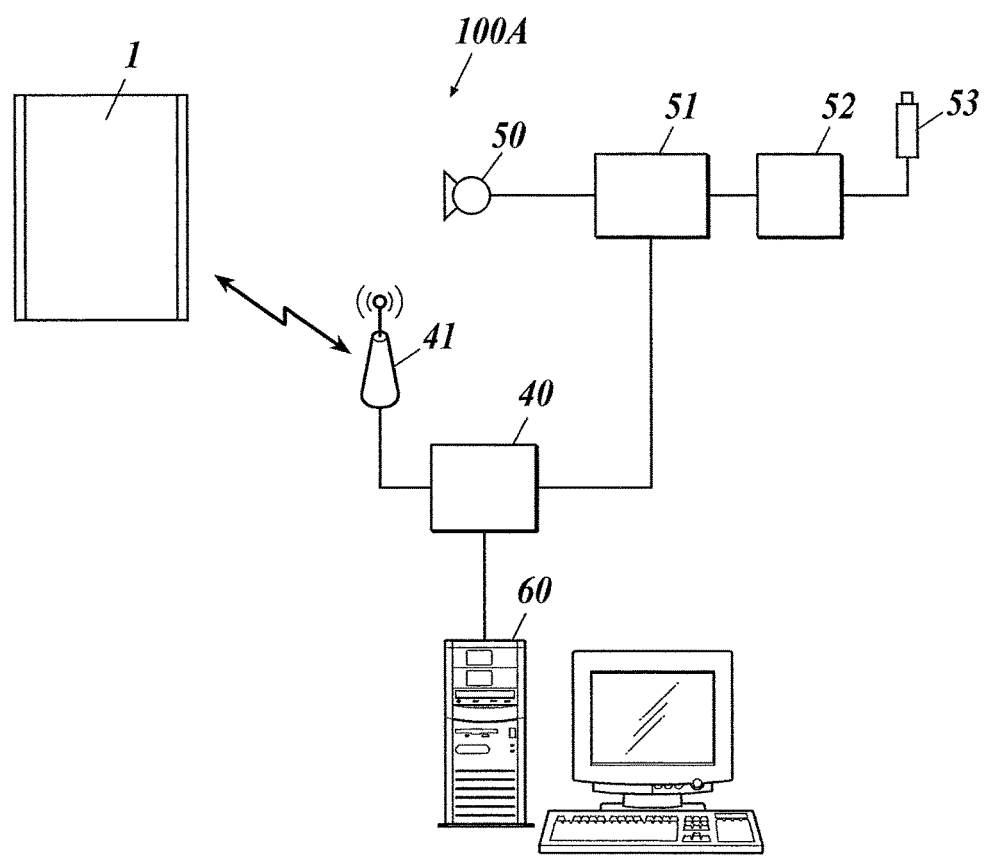
FIG. 7 illustrates an example configuration of a traditional system for capturing images through cooperation between a radiographic image capturing apparatus and a radiation irradiating apparatus.

Many radiologists press down the first button SW1 and then the second button SW2 of the exposure switch 53 with a time interval (see FIG. 6A), whereas some radiologists substantially simultaneously press down the first and second buttons SW1 and SW2 of the exposure switch 53 (see FIG. 6B).

In either case, the waiting time Tw is calculated from the delay time ΔT according to Expression (2) below. With reference to FIGS. 6A and 6B, the radiographic image capturing apparatus 1 can thus appropriately shift to the charge accumulating mode a predetermined time α before the start of radiation emission from the radiation irradiating apparatus 50.

$$Tw = \Delta T - (T2 - T1) - \alpha \quad (2)$$

In Expression (2), T1 indicates the time when the repeater 40 receives the activation signal from the exposure switch 53 after the first-step manipulation (halfway pressing operation) to the exposure switch 53, and T2 indicates the time when the repeater 40 receives the radiation start signal from the exposure switch 53 after the second-step manipulation (all-the-way pressing operation) to the exposure switch 53. In FIG. 6B, the difference between T1 and T2 is substantially 0. The predetermined time α may be 0.

The repeater 40 or the console 60 may function as a waiting time calculating device for calculating the waiting time Tw. In the case of calculation at the console 60, the repeater 40 transmits information on the time T1 of reception of the activation signal from the exposure switch 53 at the repeater 40, and information on the time T2 of reception of the radiation start signal from the exposure switch 53 at the repeater 40, to the console 60.

The repeater 40 and/or the console 60 may be constructed to calculate the waiting time Tw based on the delay time $\Delta T$ and the times T1 and T2, and to transmit the radiation start signal to the radiographic image capturing apparatus 1 at the time when the calculated waiting time Tw has elapsed after the second-step manipulation (all-the-way pressing operation) is executed to the exposure switch 53 and the repeater 40 receives the radiation start signal from the exposure switch 53 at the time T2. In this case, when receiving the radiation start signal, the radiographic image capturing apparatus 1 halts the resetting process for the radiation detecting elements 7 to shift to the charge accumulating mode, as described above.

Alternatively, the repeater 40 and/or the console 60 may transmit the waiting time Tw to the radiographic image capturing apparatus 1 after calculating the waiting time Tw from the delay time $\Delta T$ and the times T1 and T2. In this case, the repeater 40 receives the radiation start signal from the exposure switch 53 at the time T2, and then immediately transfers the radiation start signal to the radiographic image capturing apparatus 1. When receiving the radiation start signal, the radiographic image capturing apparatus 1 waits only for the waiting time Tw, and then halts the resetting process for the radiation detecting elements 7 to shift to the charge accumulating mode.

Alternatively, the waiting time Tw may be calculated at the control unit 22 of the radiographic image capturing apparatus 1. In this case, in response to the reception of the activation and radiation start signal from the repeater 40, the control unit 22 of the radiographic image capturing apparatus 1 calculates the waiting time Tw from the delay time $\Delta T$ and the times T1 and T2 of reception of the above activation and radiation start signals, respectively. The control unit 22 waits for the calculated waiting time Tw after the reception of the radiation start signal from the repeater 40 at the time T2, and then controls the radiographic image capturing apparatus 1 to halt the resetting process for the radiation detecting elements 7 and shift to the charge accumulating mode.

In any case, if the calculated waiting time Tw is 0 or negative, the radiographic image capturing apparatus 1 halts the resetting process for the radiation detecting elements 7 to shift to the charge accumulating mode immediately after the reception of the radiation start signal.

According to the above configuration, the radiographic image capturing apparatus 1 can shift to the charge accumulating mode at an appropriate timing regardless of whether the radiologist presses down the first and second buttons SW1 and SW2 of the exposure switch 53 with a time interval or simultaneously. This configuration can certainly avoid the problems illustrated in FIG. 11. The radiation irradiating apparatus 50 can thereby appropriately emit radiation during the charge accumulating mode of the radiographic image capturing apparatus 1.

Application of this Embodiment

Some radiographic image capturing apparatuses 1 are capable of autonomously detecting the start of radiation emission from the radiation irradiating apparatus 50. Such a radiographic image capturing apparatus 1 may also be applied to the image acquisition in the radiographic image capturing system 100 according to the embodiment.

The start of radiation emission may be detected with an x-ray sensor, for example. The start of radiation emission may also be detected based on an increase in the current in the bias lines 9 (see FIG. 2), the electric charges in the radiation detecting elements 7, or the electric charges leaking into the signal lines 6 through the TFTs 8 after the irradiation of the radiographic image capturing apparatus 1 with radiation, relative to that before the irradiation (see Japanese Patent Application Laid-Open Publication No. 2009-219538, International Publication No. WO 2011/152093, and International Publication No. WO 2011/135917). Alternatively, predetermined one or more of the radiation detecting elements 7 in the radiographic image capturing apparatus 1 may detect the start of radiation emission. The radiographic image capturing apparatus 1 may autonomously detect the start of emission by any other means.

By using the information on autonomously-detected start of radiation emission from the radiation irradiating apparatus 50 at the radiographic image capturing apparatus 1, a delay time (hereinafter referred to as "second delay time $\Delta T^*$" to be distinguishable from the above delay time $\Delta T$) may be determined by the above calculation.

The detail will now be explained. Although the second delay time $\Delta T^*$ is calculated at the console 60 in the explanation below, the second delay time $\Delta T^*$ may also be calculated at the control unit 22 of the radiographic image capturing apparatus 1 or the microcomputer (not shown) installed in the repeater 40. The explanation below also holds true for the latter case.

The console 60 stores the delay time $\Delta T$ preliminarily calculated as explained above or a pre-set default delay time $\Delta T$ as a first delay time $\Delta T$ in the storage unit 63 (see FIG. 3).

When the exposure switch 53 transmits the activation signal in response to the halfway pressing operation of the exposure switch 53 by pressing down the first button SW1, the repeater 40 transfers the received activation signal or a new activation signal upon reception of the activation signal. The repeater 40 also transmits information on the time of reception of the activation signal to the console 60. The console 60 receives this temporal information from the repeater 40, and then records the time as the time T1 of reception of the activation signal from the exposure switch 53 at the repeater 40.

In response to the detection of the start of the radiation emission from the radiation irradiating apparatus 50, the control unit 22 of the radiographic image capturing apparatus 1 transmits information on the time of detection of the start of radiation emission to the console 60 via the repeater 40. The console 60 receives this temporal information from the radiographic image capturing apparatus 1, and records the time as a time Tr* when the radiographic image capturing apparatus 1 detects the start of radiation emission from the radiation irradiating apparatus 50.

The console 60 is constructed to calculate the difference between the time T1 and the above time Tr* according to Expression (3) below, as the second delay time $\Delta T^*$. According to the configuration, the delay time in the radiation irradiating apparatus 50 can be determined by a simple procedure by effectively using the function of the radiographic image capturing apparatus 1 to autonomously detect the start of radiation emission from the radiation irradiating apparatus 50.

$$\Delta T^* = Tr^* - T1 \quad (3)$$

On the calculated second delay time $\Delta T^*$, the first delay time $\Delta T$ stored in the storage unit 63 (see FIG. 3) of the console 60 may be updated, for example.

Alternatively, the second delay times $\Delta T^*$ calculated in the past may be preliminarily stored, and the currently calculated second delay time $\Delta T^*$ may be compared with any one of the stored second delay times $\Delta T^*$ or the average (moving average, in this case) of a predetermined number of recently calculated values of the stored second delay times $\Delta T^*$ to obtain a difference their between, for example. In this case, the first delay time $\Delta T$ may be updated if the absolute value of the difference is equal to or larger than a predetermined value.

The absolute value of the difference between the currently calculated second delay time $\Delta T^*$ and the first delay time $\Delta T$ stored in the storage unit 63 may be equal to or larger than a predetermined threshold, which indicates any abnormality in the radiation irradiating apparatus 50. In this case, the display unit 61 of the console 60 may notify the user (e.g., radiologist) of this situation with a certain display, for example. This configuration can detect abnormality in the radiation irradiating apparatus 50 based on the second delay time $\Delta T^*$.

The above embodiments should not be construed to limit the present invention and may be appropriately modified within the gist of the present invention.

What is claimed is:

1. A radiographic image capturing system comprising:
   a radiation irradiating apparatus which emits radiation and provides notification of radiation emission while emitting the radiation;
   a radiographic image capturing apparatus which includes a plurality of radiation detecting elements disposed in a two-dimensional matrix and executes an image data reading process to read one or more electric charges accumulated in the respective radiation detecting elements as image data;
   an exposure switch capable of two-step manipulations, the exposure switch transmitting an activation signal in response to a first-step manipulation and transmitting a radiation start signal in response to a second-step manipulation;
   a signal transceiver which receives the activation signal transmitted from the exposure switch and transfers the received activation signal to the radiation irradiating apparatus;
   a delay time calculating device which calculates, as a delay time, a difference between a time of reception of the activation signal from the exposure switch at the signal transceiver and a time of start of the notification of radiation emission at the radiation irradiating apparatus; and
   a waiting time calculating device which calculates a waiting time based on the delay time;
   wherein the signal transceiver receives the radiation start signal transmitted from the exposure switch; and
   wherein the radiographic image capturing apparatus shifts to a charge accumulating mode after elapse of the waiting time from reception of the radiation start signal at the signal transceiver during image capture, the charge accumulating mode involving accumulation of the electric charges in the radiation detecting elements.

2. The radiographic image capturing system of claim 1, wherein the waiting time calculating device calculates the waiting time by subtracting, from the delay time, a difference between a time of reception of the radiation start signal from the exposure switch at the signal transceiver and the time of reception of the activation signal from the exposure switch at the signal transceiver.

3. The radiographic image capturing system of claim 1, wherein the radiation irradiating apparatus provides the notification of radiation emission with at least one of sound, illumination, and vibration.

4. A radiographic image capturing system comprising:
   a radiation irradiating apparatus which emits radiation and provides notification of radiation emission while emitting the radiation;
   a radiographic image capturing apparatus which includes a plurality of radiation detecting elements disposed in a two-dimensional matrix and executes an image data reading process to read one or more electric charges accumulated in the respective radiation detecting elements as image data;
   an exposure switch capable of two-step manipulations, the exposure switch transmitting an activation signal in response to a first-step manipulation and transmitting a radiation start signal in response to a second-step manipulation;
   a signal transceiver which receives the activation signal transmitted from the exposure switch and transfers the received activation signal to the radiation irradiating apparatus; and
   a delay time calculating device which calculates, as a delay time, a difference between a time of reception of the activation signal from the exposure switch at the signal transceiver and a time of start of the notification of radiation emission at the radiation irradiating apparatus;
   wherein the radiographic image capturing apparatus autonomously detects a start of radiation emission from the radiation irradiating apparatus, and
   wherein the delay time calculating device: stores the calculated delay time in a storage device; calculates a second delay time as a difference between the time of reception of the activation signal from the exposure switch at the signal transceiver and a time of detection of the start of radiation emission from the radiation irradiating apparatus at the radiographic image capturing apparatus during image capture; and at least one of updates the delay time stored in the storage device with the calculated second delay time and provides a notification to a user if an absolute value of a difference between the calculated second delay time and the delay time stored in the storage device becomes equal to or larger than a predetermined threshold.

5. A radiographic image capturing system comprising:
   a radiation irradiating apparatus which emits radiation;
   a radiographic image capturing apparatus which includes a plurality of radiation detecting elements disposed in a two-dimensional matrix, executes an image data reading process to read one or more electric charges accumulated in the respective radiation detecting elements as image data, and autonomously detects a start of radiation emission from the radiation irradiating apparatus;
   an exposure switch which transmits an activation signal to make the radiation irradiating apparatus activated;
   a signal transceiver which at least one of receives the activation signal transmitted from the exposure switch and transfers the received activation signal and transfers a new activation signal upon reception of the activation signal; and a delay time calculating device which calculates a delay time as a difference between a time of reception of the activation signal from the exposure switch at the signal transceiver and a time of detection of the start of radiation emission from the radiation irradiating apparatus at the radiographic image capturing apparatus, wherein the delay time calculating device: stores one of a preliminarily calculated delay time and a preset delay time as a first delay time in a storage device; calculates, as a second delay time, the delay time which is the difference between the time of reception of the activation signal from the exposure switch at the signal transceiver and the time of detection of the start of radiation emission from the radiation irradiating apparatus at the radiographic image capturing apparatus during image capture; and at least one of updates the first delay time stored in the storage device with the second delay time and provides a notification to a user if an absolute value of a difference between the calculated second delay time and the first delay time stored in the storage device becomes equal to or larger than a predetermined threshold.

6. The radiographic image capturing system of claim 1, further comprising:

a repeater; and a console, wherein the delay time calculating device is installed in at least one of the radiographic image capturing apparatus, the repeater, and the console.

* * * * *